(12) United States Patent
Sourice et al.

(10) Patent No.: US 11,199,482 B2
(45) Date of Patent: Dec. 14, 2021

(54) FLUID SAMPLING PROBE

(71) Applicant: EXCELLENCE LOGGING FRANCE, Sannois (FR)

(72) Inventors: Louis Sourice, Niel sur Mer (FR); Samuel Giraudet, Courbevoie (FR)

(73) Assignee: EXCELLENCE LOGGING FRANCE, Sannois (FR)

( * ) Notice: Subject to any disclaimer, the term of this patent is extended or adjusted under 35 U.S.C. 154(b) by 285 days.

(21) Appl. No.: 16/342,768

(22) PCT Filed: Oct. 17, 2017

(86) PCT No.: PCT/EP2017/076475
§ 371 (c)(1),
(2) Date: Jul. 22, 2019

(87) PCT Pub. No.: WO2018/073249
PCT Pub. Date: Apr. 26, 2018

(65) Prior Publication Data
US 2019/0346350 A1    Nov. 14, 2019

(30) Foreign Application Priority Data
Oct. 17, 2016 (FR) .................................... 16 60025

(51) Int. Cl.
| | |
|---|---|
| *G01N 1/40* | (2006.01) |
| *G01N 1/14* | (2006.01) |
| *G01N 33/28* | (2006.01) |
| *E21B 21/01* | (2006.01) |
| *E21B 49/00* | (2006.01) |

(52) U.S. Cl.
CPC ........... *G01N 1/4077* (2013.01); *E21B 21/01* (2013.01); *E21B 49/005* (2013.01); *G01N 1/14* (2013.01); *G01N 33/2823* (2013.01); *G01N 2001/4088* (2013.01)

(58) Field of Classification Search
CPC ..... G01N 1/4077; G01N 1/14; G01N 33/2823
USPC ........................................................ 73/64.56
See application file for complete search history.

(56) References Cited

U.S. PATENT DOCUMENTS

| | | |
|---|---|---|
| 2011/0308787 A1 | 12/2011 | Briquet |
| 2012/0160514 A1 | 6/2012 | Evans, II |
| 2013/0032527 A1 | 2/2013 | Calleri |

(Continued)

OTHER PUBLICATIONS

Rapport de Recherche Preliminaire issued in corresponding French Patent Application No. FR 1660025 dated Jul. 31, 2017.

(Continued)

*Primary Examiner* — John Fitzgerald
*Assistant Examiner* — Rodney T Frank
(74) *Attorney, Agent, or Firm* — Troutman Pepper Hamilton Sanders LLP

(57) ABSTRACT

The invention relates to a probe for sampling a drilling fluid comprising a handle extending along an axis, and a sampling head located at a first end of the handle, the head defining an inner space opening outward through an opening. The head comprises a filtration device comprising a filtering wall disposed through the opening; and an extraction duct extending into the handle and opening into the inner space of the head. The filtration device comprises a cleaning blade designed to sweep an outer face of the filtering wall, the blade being mounted to move in translation in a direction parallel to the axis.

15 Claims, 6 Drawing Sheets

(56) References Cited

U.S. PATENT DOCUMENTS

| | | | |
|---|---|---|---|
| 2013/0062051 A1* | 3/2013 | Brennan | E21B 49/10 |
| | | | 166/120 |
| 2014/0131031 A1 | 5/2014 | Tingat Cody | |
| 2014/0144625 A1* | 5/2014 | Corre | E21B 49/08 |
| | | | 166/264 |
| 2014/0216176 A1* | 8/2014 | Kimour | E21B 21/01 |
| | | | 73/863.23 |

OTHER PUBLICATIONS

Rapport de Recherche Internationale issued in corresponding International Patent Application No. PCT/EP2017/076475 dated Jan. 31, 2018.

* cited by examiner

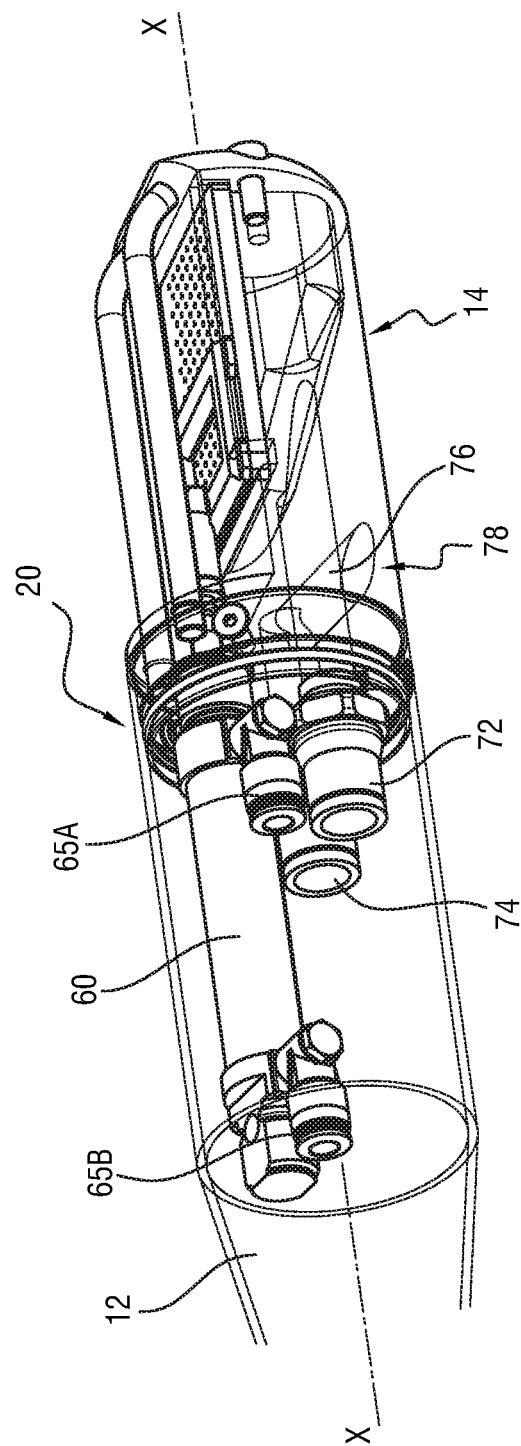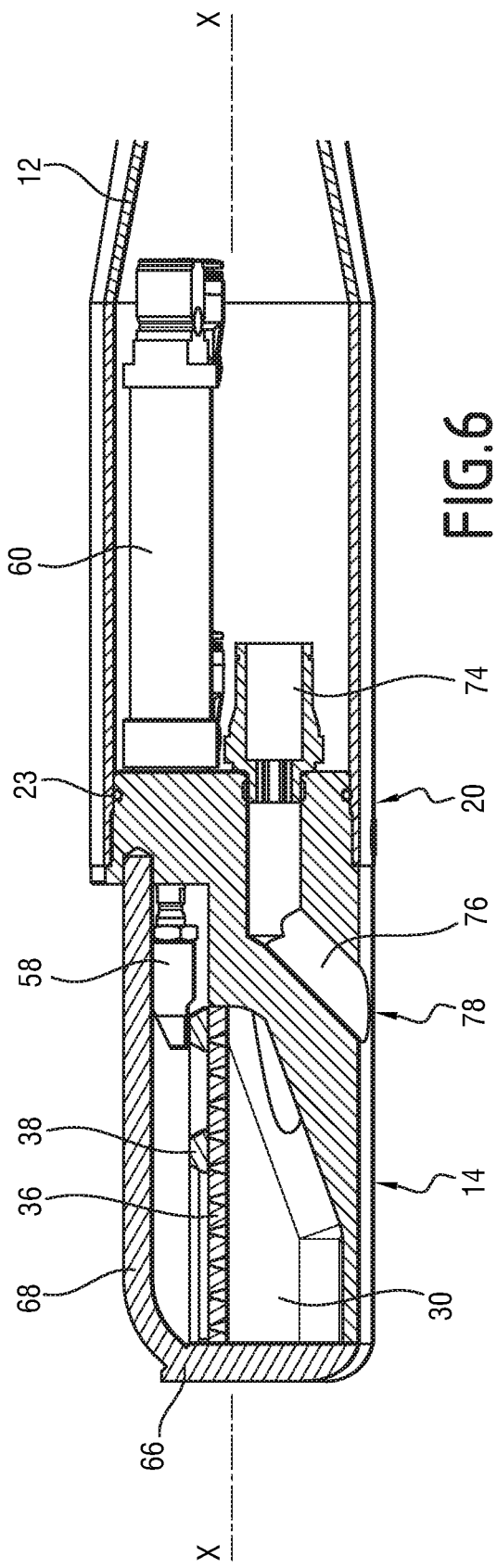

FLUID SAMPLING PROBE

CROSS REFERENCE TO RELATED APPLICATION

This is a U.S. National Phase Application under 35 U.S.C. § 371 of International Patent Application No. PCT/EP2017/076475, filed Oct. 17, 2017, which claims priority of French Patent Application No. 16 60025, filed Oct. 17, 2016. The entire contents of both applications are hereby incorporated by reference.

FIELD OF TECHNOLOGY

The present invention relates to a probe for sampling drilling fluid comprising:
- a handle extending along an axis;
- a sampling head at a first end of the handle, the head defining an internal space opening outwards through an opening, the head comprising a filtration device comprising a filtering wall disposed through the opening; and
- an extraction duct extending into the handle and opening into the internal space of the head. The invention also relates to a fluid sampling system and a petroleum drilling installation.

BACKGROUND

During an oil drilling operation, fluids are injected continuously from the surface installations to the bottom of the well, in particular to cool and lubricate the drilling tools at the bottom of the well. These fluids then rise to the surface, carrying with them rock debris torn off during drilling. In addition, the fluids are exposed to the rock formations crossed, and may be loaded with hydrocarbons according to the contents of the formations encountered.

It is known to analyze drilling fluids at the outlet of wells in order to obtain information on the nature of the rock formations and their contents, in particular in hydrocarbons and in dissolved gases.

The known devices for analyzing drilling fluids generally comprise a sampling device inserted in the flow of drilling fluids in the well outlet, and connected to a pump by a flexible duct. The pump and the fluid analysis devices are generally located away from the circulation line for safety reasons, but also in order to disturb as little as possible the drilling and pumping operations.

Given the nature of the fluids, it is necessary for this device to have an inlet filter in order to prevent rock debris from clogging the sampling line. In addition, because drilling fluids contain a lot of solid particles, the filter must be cleaned regularly to prevent it from clogging.

It is known, for example in U.S. Pat. No. 5,090,256, to use a rotating cleaning blade to continuously clean the filter during extraction of drilling fluids. This blade is set in motion by a motor located far from the fluid circulation line with the engine torque being transmitted by a Bowden cable.

This device therefore comprises two separate casings and has high rigidity, which complicates its insertion into a closed circulation line. In addition, the Bowden cable is subject to heavy wear, which poses a risk of mechanical damage.

The document US 2014/0216176 describes an improved sampling device in the form of a closed metal probe that is easily insertable into a sealed circulation line. This device also comprises a filter cleaned by a rotating blade driven by a Bowden cable.

This device may be further improved. The present invention aims to provide a sampling probe with reduced use constraints compared to previous devices.

SUMMARY

Thus, the object of the invention is a sampling probe of the aforementioned type, characterized in that the filtration device comprises a cleaning blade designed to sweep an outer face of the filtering wall, the blade being mounted to be mobile in translation in a direction parallel to the axis.

According to particular embodiments, the probe according to the invention has one or more of the following characteristics, taken in isolation or in any technically feasible combination:
- the filtration device comprises a jack designed to move the blade over the outer face of the filtering wall;
- the filtration device comprises at least one pneumatic duct contained in the handle and opening into the cylinder;
- the blade has a central opening;
- the blade has contact surfaces with the filtering wall only at the lateral edges of the blade;
- the filtering wall has a plurality of orifices having a first transverse section situated in the vicinity of the internal space, with an area greater than the area of a second transverse section located outside the first transverse section;
- the orifices have a frustoconical shape;
- the blade and the filtering surface are assembled in grooves of the head, the filtration device comprising a device for holding the blade and the filtering wall removably attached to the head;
- the outer face of the filtering wall has a normal that is substantially perpendicular to the axis; and
- the probe comprises a fluid reinjection duct contained in the handle and opening into the outside through an outlet located at the head opposite the filtering wall.

The invention also relates to a fluid sampling system, comprising:
- a probe as described above, the head of the probe being intended to be placed in a fluid to be sampled;
- an extraction pump fluidly connected to a free end of the extraction duct of the probe;
- a device for analyzing the fluid, fluidly connected to an outlet of the extraction pump.

According to a particular embodiment, the system according to the invention comprises the following characteristic:
- the system comprises a feedback pump fluidly connected to the reinjection line, the outlet orifice being located downstream of the filtering wall with respect to a fluid flow direction.

The invention also relates to a petroleum drilling installation, comprising a fluid sampling system as described above and a duct in which a drilling fluid circulates, the head being inserted into the duct and immersed in the fluid.

According to particular embodiments, the installation according to the invention has one or more of the following characteristics, taken in isolation or in any technically feasible combination:
- the head is oriented in the duct so that the outer face of the filtering wall faces a flow direction of the drilling fluid; and the installation comprises a fluid extraction pump, connected to the extraction duct, a gas separation chamber, and a gas analysis device in the separation chamber.

The invention also relates to a drill fluid sampling probe comprising:
- a handle extending along an axis;
- a sampling head at a first end of the handle, the head defining an internal space opening outwards through an opening, the head comprising a filtration device comprising a filtering wall disposed through the opening; and
- an extraction duct extending into the handle and opening into the internal space of the head, characterized in that the probe comprises a fluid reinjection duct contained in the handle and opening into the outside through an outlet located at the head, opposite the filtering wall.

The probe does not necessarily include a cleaning blade.

BRIEF DESCRIPTION OF THE DRAWINGS

The invention will be better understood upon reading the description which follows, given solely by way of example and with reference to the appended drawings, wherein:

FIG. 5 shows a rear view of the head of FIGS. 2 to 4;

FIG. 6 shows a sectional view of the head of FIGS. 2 to 5; and

DETAILED DESCRIPTION

Figure 1:
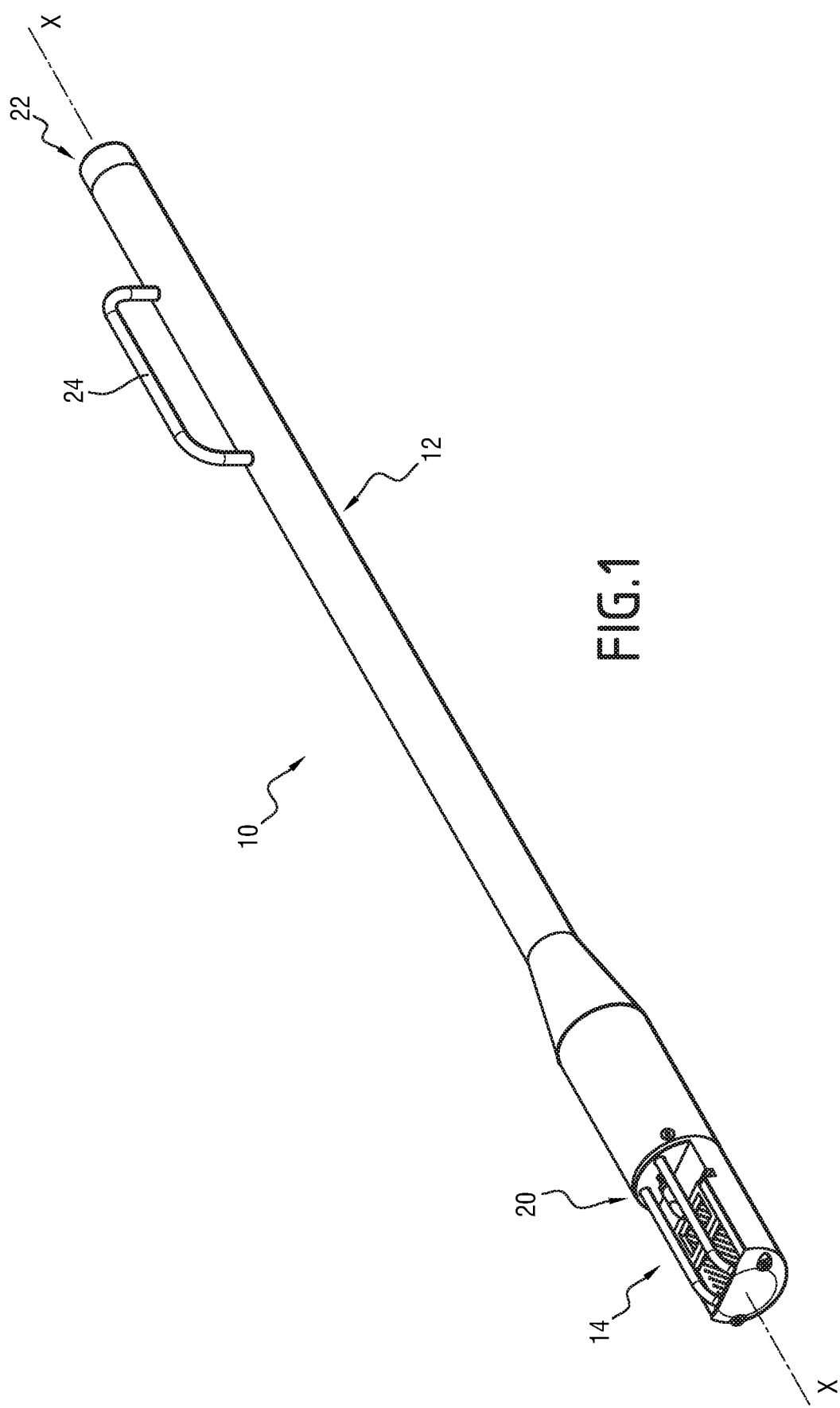
FIG. 1 shows a perspective view of a probe according to the invention.

A probe 10 for fluid sampling according to the invention is shown in FIG. 1.

Figure 7:
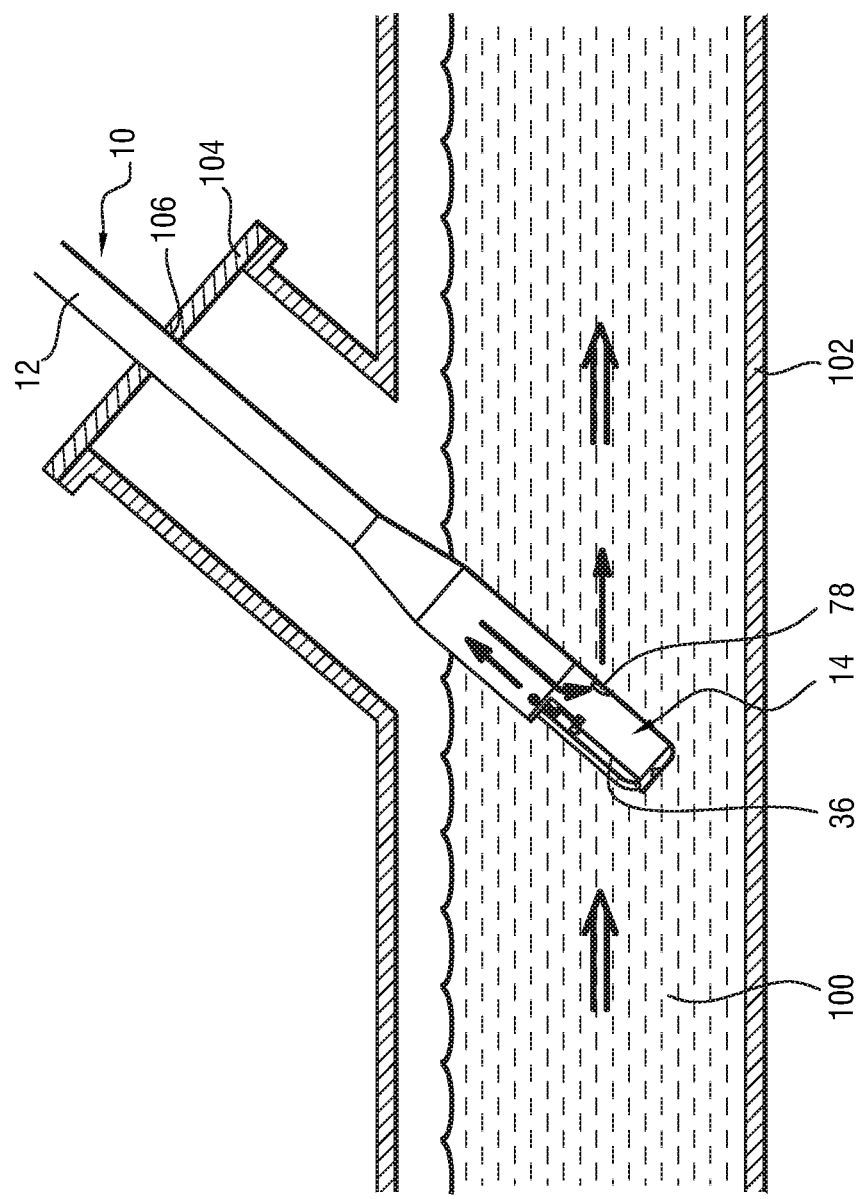
FIG. 7 shows a lateral sectional view of a circulation duct receiving the probe of FIG. 1.

The probe 10 is intended to be inserted in a duct 102, visible in FIG. 7, for sampling a fluid 100 present in the duct 102. The duct 102 is, for example, located at the outlet of a well being drilled to recover a fluid leaving the well. In a variant, the duct 102 is situated at the inlet of the well and receives a fluid intended to be injected into the well.

With reference to FIG. 1, the probe 10 comprises a handle 12 and a sampling head 14 attached to the handle 12, as well as an extraction duct 16 and a reinjection duct 18 contained in the shaft 12.

The handle 12 is a hollow tube, for example metallic. It has a first end 20 and a second end 22. The handle 12 extends along a longitudinal axis X-X.

The handle 12 defines an internal volume in which the extraction duct 16 and the reinjection duct 18 extend from the first end 20 to the second end 22.

The handle 12 is flared at the first end 20 and in which is fitted the head 14. The head 14 is provided with an O-ring 23 located between the flare of the first end 20 and the head 14 to ensure sealing of the probe 10.

Advantageously, the handle 12 has a grip 24 close to the second end 22, to facilitate the handling of the probe 10 by a user.

Figure 2:
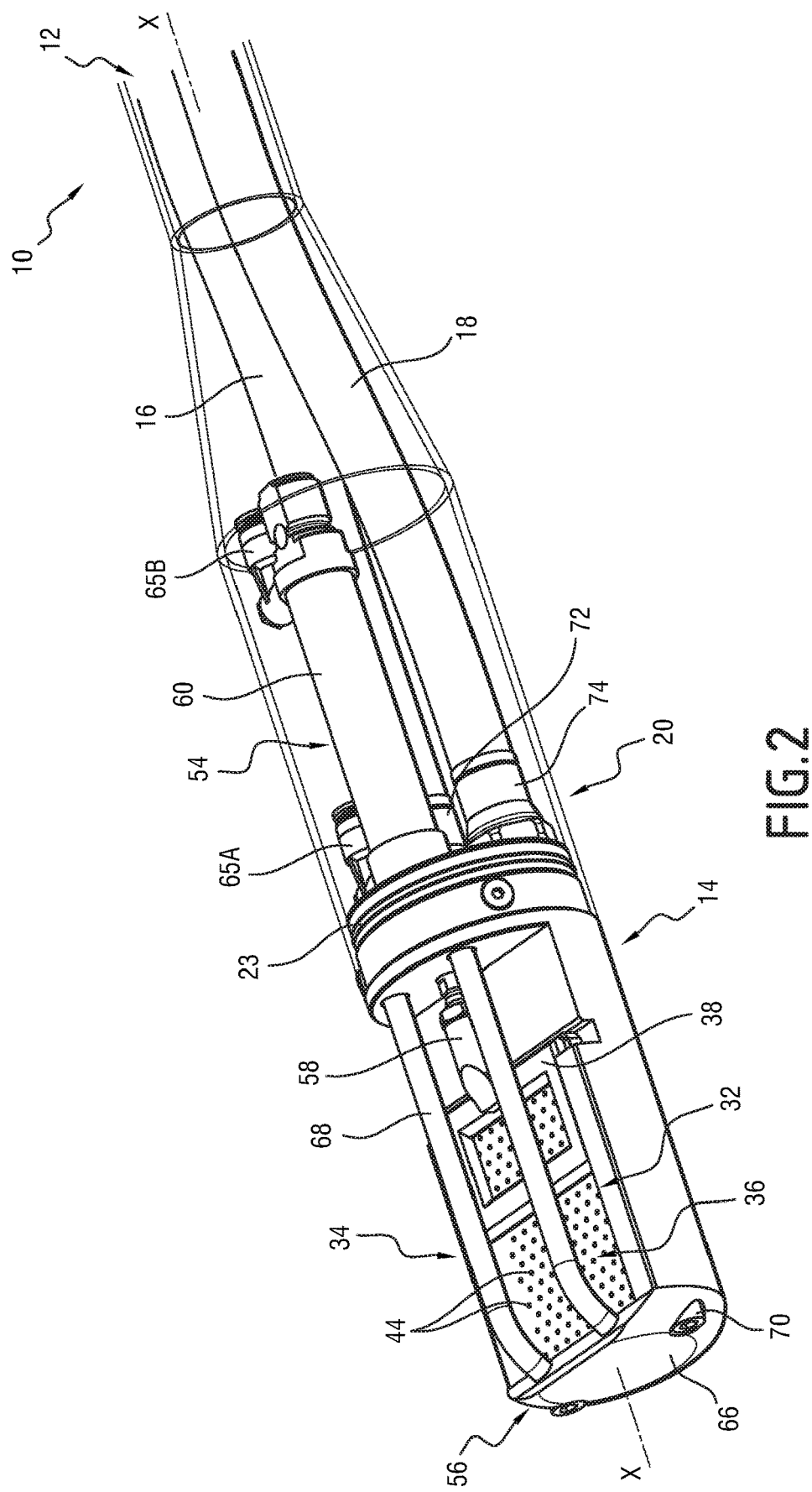
FIG. 2 shows a perspective view of a head of the probe of FIG. 1.
Figure 3:
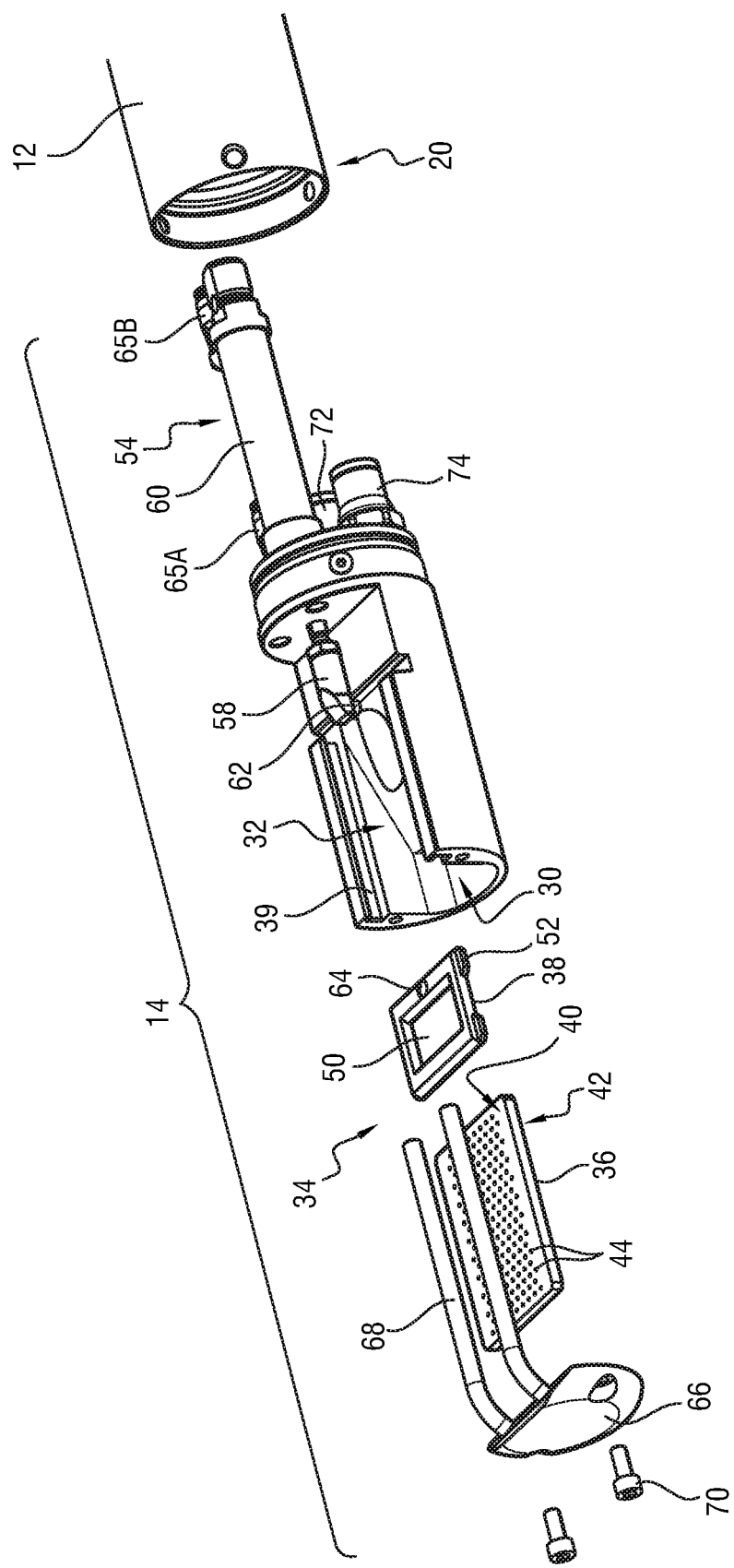
FIG. 3 shows an exploded view of the head of FIG. 2.

The head 14 is a hollow metal shell, shown in FIGS. 2 and 3, defining an internal space 30 opening outwards through an opening 32. The head 14 is fixed to the first end 20 of the handle 12 and extends substantially along the longitudinal axis X-X. The head 14 has a truncated cylinder shape in a plane passing through two generatices.

Subsequently, positioned internally and externally is understood to mean respectively closer and further away from the internal space 30 of the head 14.

The opening 32 opens into the internal space 30 and outside the head 14. The opening 32 may be, for example, rectangular, and have a normal oriented substantially perpendicular to the longitudinal axis X-X.

The head 14 defines, at the edges of the opening 32, grooves 39 parallel to the X-X axis opening at the free end of the head 14.

The head 14 comprises a filtration device 34, intended to prevent the passage through the opening 32 of solid objects having a size greater than a filtration threshold.

The filtration device 34 comprises a filtering wall 36 disposed through the opening 32 and a cleaning blade 38 designed to clean the filtering wall 36. It further comprises a jack 54 actuating the blade 38, as well as a holding device 56 for the blade 38 as well as the filtering wall 36.

Figure 4:
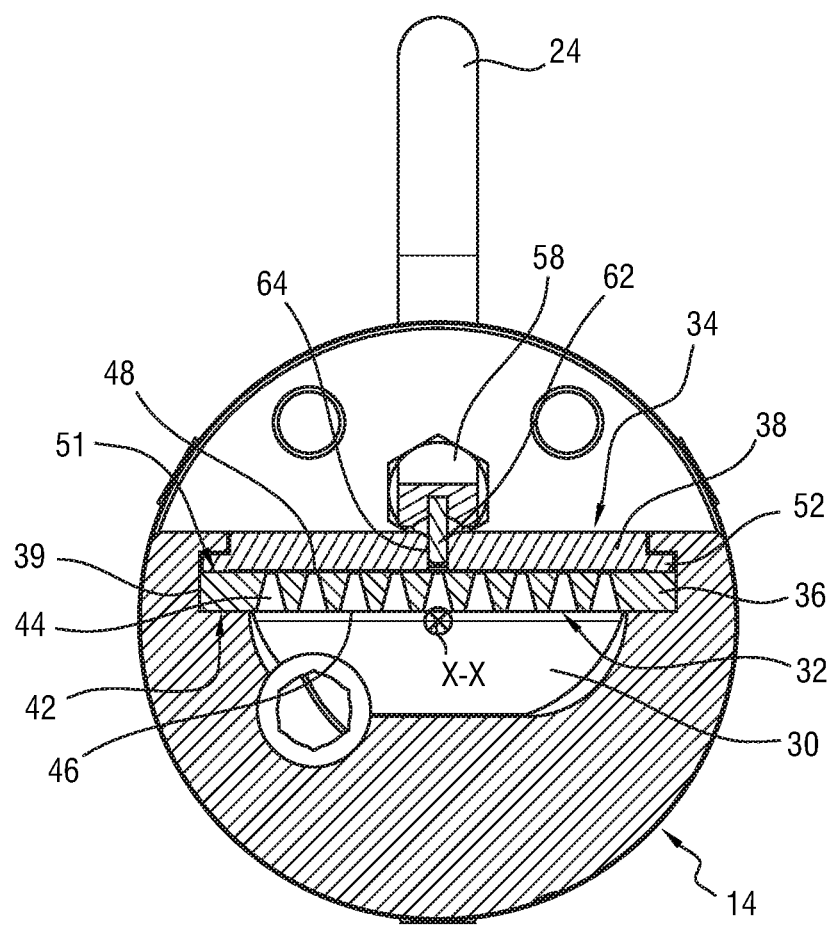
FIG. 4 shows a sectional view of a filtration device of the head of FIGS. 2 and 3.

As shown in FIGS. 3 and 4, the filtering wall 36 and the blade 38 are engaged in the grooves 39 of the head 14.

The filtering wall 36 is a substantially rectangular plate having an outer face 40 and an inner face 42 and a plurality of orifices 44 passing through the filtering wall 36, and opening on the outer face 40 and on the inner face 42.

The orifices 44 have a first transverse section 46 located in the vicinity of the internal space 30, for example at the inner face 42, and a second transverse section 48 located away from the first transverse section 46, for example at the outer face 40.

In the example shown, the orifices 44 have a frustoconical shape, having a narrow section at the outer face 40 and a wider section at the inner face 42. The area of the wider section is greater than the area of the narrow section.

The geometry of the orifices 44 prevents the accumulation of solid particles in each orifice 44 as the fluid flows, and thus prevents the orifice 44 from clogging.

Referring to FIG. 3, the cleaning blade 38 is designed to sweep the outer face 40 of the filtering wall 36 to remove solid particles that are deposited there. The blade 38 is of substantially rectangular shape, with a central opening 50.

The central opening 50 increases the effective length of the blade 38 for cleaning the filtering wall 36. In fact, the cleaning of the filtering wall 38 is performed both by an outer edge and by an inner edge of the blade 38 in both directions of movement of the blade 38.

The blade 38 has contact surfaces 51 on a lower face, at the lateral edges of the blade 38. Lateral is understood to mean the edges of the blade 38 which are parallel to the direction of movement.

The contact surfaces 51 are reliefs protruding from the lower face of the blade 38, and which bear on the upper face 40 of the filtering wall 36. Thus, the blade 38 is not in direct contact with the filtering wall 36 at the level of the transverse edges in the direction of movement.

The blade 38 also has protuberances 52 protruding from the lateral edges of the blade 38.

The protuberances 52 are engaged externally in the grooves 39 with respect to the filtering wall 36, in order to guide the movement of the blade 38 in translation along the X-X axis, on the filtering wall 36.

The jack 54 is a pneumatic actuating device able to move the blade 38 in translation along the outer face 40 of the filtering wall 36. The jack 54 comprises an arm 58 extending parallel to the axis X-X, and a piston 60 in which the arm 58 is slidably mounted.

The arm 58 is provided with a lug 62 at its free end, the lug 62 being engaged in a cavity 64 located on the blade 38.

The piston 60 is designed to move the arm 58 along the X-X axis between a retracted position and an extended position. For this purpose, the piston 60 has a front socket 65A and a rear socket 65B opening into an inner space of the piston 60.

The front socket 65A and rear socket 65B are fluidly connected to pneumatic lines containing compressed air, extending inside the sleeve 12 and opening into the interior space of the piston 60.

The retracted and extended positions correspond to the end positions of the arm 58 in the piston 60. In the extended position, the blade 38 is further away from the piston 60 than in the retracted position. The blade 38 deploys facing a first region of the filtering wall 36 and reveals a second region of the filtering wall 36. In the retracted position, the blade 38 extends opposite the second region and leaves the first region at least partly open.

The length of the arm 58 is designed so that the blade 38 does not come into contact with the holding device 56 when the arm 58 is in the extended position.

The application in the front socket 65A of a pressure greater than the pressure in the rear socket 65B moves the arm 58 to its retracted position. Conversely, the application in the rear socket 65B of a pressure greater than the pressure in the front socket 65A moves the arm 58 to its extended position.

The holding device 56 comprises a cover 66 and two protective probes 68 attached to the cover 66 at a respective end.

The cover 66 closes the inner space 30 of the head and has two holes in which are inserted two fixing screws 70 to removably assemble the holding device to the head.

The holding device 66 blocks the filtering wall 36 and the blade 38 in the grooves 39 when assembled to the head 14, and may be disassembled in order to disassemble the filtering wall 36 and the blade 38 for cleaning or replacement.

The protection rods 68 extend outwards from the cover 66 with respect to the filtering wall 36 and to the blade 38, in order to protect them against external shocks. In the example shown, the protection probes 68 extend substantially parallel to the X-X axis.

The extraction duct 16 is advantageously flexible. It is intended to transport the fluid from the head 14 and along the handle 12. The extraction duct 16 extends inside the handle 12. The extraction duct 16 opens into the inner space 30 of the head 14 through an extraction socket 72 at a first end. It may be fluidly connected to an extraction pump at a second end.

The application of an under pressure in the extraction duct sucks out the contents of the inner space 30 and thus takes fluid from the outside of the head 14 and through the orifices of the filtering wall 36.

The reinjection duct 18 is advantageously flexible. It is intended to transport the fluid through the handle 12. The reinjection duct 18 extends inside the handle 12. The reinjection duct is fluidly connected to a reinjection socket 74 at a first end, and is designed to be fluidly connected to a reinjection pump at a second end.

The feedback socket 74 is located at the input of a feedback channel 76 passing through the head 14.

The reinjection channel 76 is a perforation in the head 14, which opens out of the probe 10 through an outlet orifice 78 located in the head 14, on the side opposite the opening 32.

In operation, the probe 10 is integrated in a fluid sampling system, which also comprises an extraction pump, a gas separation chamber, an analysis device, and a reinjection pump.

The head 14 of the probe 10 is immersed in a fluid 100 to be sampled. The fluid 100 flows, for example, in a duct 102 in a flow direction as shown in FIG. 7.

The extraction pump is fluidly connected to the extraction line 16, and applies an under pressure in the inner space 30 of the head 14 to draw a sample of fluid through the orifices 44 of the filtering wall 36.

The gas separation chamber is capable of agitating the fluid sample to extract the gases.

The analysis device is fluidly connected to a separation outlet. The analysis device is designed to perform one or more measurements on the dissolved gases in the fluid sample, for example to measure the content of different gases in the fluid.

The feedback pump is fluidly connected to an output of the analysis device and reinjects the analyzed fluid sample, through the feedback line 18 and the outlet port 78, into the line 102.

The probe 10 is so oriented in the duct 102 that the outer face 40 of the filtering wall 36 faces the flow direction of the fluid 100 in the duct 102, and that the outlet orifice 78 is located downstream of the filtering wall 36 with respect to the flow direction. Thus, there is no loop measurement of the same sample of fluid, which could distort the results of the analyzes.

The fluid 100 may be, for example, a drilling fluid, while the duct 102 may be, for example, part of a petroleum drilling rig. The fluid 100 is analyzed at the outlet of the well, and contains dissolved hydrocarbons, the concentration of which in the drilling fluid 100 is to be measured.

The duct 102 is then advantageously a closed duct to prevent the emission of flammable vapors at the drilling site.

The probe 10, thanks to the simple tubular shape of the handle 12, may be inserted in the closed duct 102 in a sealed manner, for example by means of a valve 104 in two parts, having a central orifice 106.

The probe 10 thus has a compact shape comprising a single tube 12, which facilitates its handling and its insertion into closed spaces. The translational movement of the blade 38 generates less mechanical wear than a conventional rotary system. In addition, the filtration device 34 is completely and simply removable, which greatly facilitates the maintenance and replacement of different parts.

The jack 54 operates solely pneumatically, while the probe 10 does not require the generation or transport of electrical energy in the vicinity of flammable or explosive hydrocarbon vapors, which has significant advantages in terms of safety of the drilling installation.

The invention claimed is:

1. A drill fluid sampling probe comprising: a handle extending along an axis; a sampling head located at a first end of the handle, the head defining an inner space opening outwards through an opening, the head comprising a filtration device comprising a filtering wall disposed through the opening; and an extraction duct extending into the handle and opening into the inner space of the head; wherein the filtration device comprises a cleaning blade designed to sweep an outer face of the filtering wall, the blade being mounted to move in translation in a parallel direction to the an extension axis of the handle, wherein the blade has a central opening.

2. The probe according to claim 1 wherein the filtration device comprises a jack designed to move the blade over the outer face of the filtering wall.

3. The probe according to claim 2, wherein the filtration device comprises at least one pneumatic duct contained in the handle and opening into the jack.

4. The probe according to claim 1, wherein the blade has contact surfaces with the filtering wall only at the lateral edges of the blade.

5. The probe according to claim 1, wherein the filtering wall has a plurality of orifices having a first cross-section adjacent the inner space, with an area greater than an area of a second cross-section spaced apart from the first cross-section.

6. The probe according to claim 5, wherein the orifices have a frustoconical shape.

7. The probe according to claim 1, wherein the blade and the filtering surface are assembled in grooves of the head, the filtering device comprising a holding device for the blade and the filtering wall removably attached to the head.

8. The probe according to claim 1, wherein the outer face of the filtering wall has a normal substantially perpendicular to the extension axis of the handle.

9. The probe according to claim 1 comprising a fluid reinjection duct contained in the handle and opening into the outside through an outlet port located at the head, opposite the filtering wall.

10. A fluid sampling system comprising:
a probe according to claim 1, the head of the probe being intended to be placed in a fluid to be sampled;
an extraction pump, fluidly connected to a free end of the extraction duct of the probe;
a device for analyzing the fluid, fluidly connected to an outlet of the extraction pump.

11. The system according to claim 10, wherein the probe comprises a fluid reinjection duct contained in the handle and opening into the outside through an outlet port located at the head, opposite the filtering wall, the system comprising a feedback pump fluidly connected to the reinjection duct, the outlet orifice being located downstream of the filtering wall with respect to a fluid flow direction.

12. An oil drilling installation comprising a system according to claim 10 and a duct in which a drilling fluid circulates, the head being inserted into the duct and immersed in the fluid.

13. The installation according to claim 12, wherein the head is oriented in the duct so that the outer face of the filtering wall faces a flow direction of the drilling fluid.

14. The installation according to claim 12, comprising a fluid extraction pump, connected to the extraction duct, a gas separation chamber, and a gas analysis device in the separation chamber.

15. A drill fluid sampling probe comprising: a handle extending along an axis; a sampling head located at a first end of the handle, the head defining an inner space opening outwards through an opening, the head comprising a filtration device comprising a filtering wall disposed through the opening; and an extraction duct extending into the handle and opening into the inner space of the head; wherein the filtration device comprises a cleaning blade designed to sweep an outer face of the filtering wall, the blade being mounted to move in translation in a parallel direction to an extension axis of the handle, the outer face of the filtering wall having a normal substantially perpendicular to the extension axis of the handle, wherein the blade has a central opening.

* * * * *